United States Patent
Wang et al.

(10) Patent No.: US 12,201,412 B2
(45) Date of Patent: Jan. 21, 2025

(54) SYSTEM AND METHOD FOR RECONSTRUCTION USING A HIGH-RESOLUTION PHASE IN MAGNETIC RESONANCE IMAGES

(71) Applicant: GE Precision Healthcare LLC, Wauwatosa, WI (US)

(72) Inventors: Xinzeng Wang, Houston, TX (US); Daniel V. Litwiller, Denver, CO (US); Arnaud Guidon, Boston, MA (US); Ersin Bayram, Houston, TX (US); Robert Marc Lebel, Calgary (CA); Tim Sprenger, Sundybyberg (SE)

(73) Assignee: GE Precision Healthcare LLC, Waukesha, WI (US)

( * ) Notice: Subject to any disclaimer, the term of this patent is extended or adjusted under 35 U.S.C. 154(b) by 468 days.

(21) Appl. No.: 17/172,644

(22) Filed: Feb. 10, 2021

(65) Prior Publication Data
US 2022/0248972 A1    Aug. 11, 2022

(51) Int. Cl.
*A61B 5/055*    (2006.01)
*A61B 5/00*    (2006.01)
*G01R 33/46*    (2006.01)
*G01R 33/48*    (2006.01)
*G01R 33/56*    (2006.01)

(52) U.S. Cl.
CPC .............. *A61B 5/055* (2013.01); *A61B 5/726* (2013.01); *A61B 5/7267* (2013.01); *G01R 33/4616* (2013.01); *G01R 33/4818* (2013.01); *G01R 33/5602* (2013.01)

(58) Field of Classification Search
CPC ....... A61B 5/055; A61B 5/726; A61B 5/7267; G01R 33/4818; G01R 33/4616; G01R 33/5602; G01R 33/4824; G01R 33/5608; G01R 33/561; G06T 11/005; G06T 7/0002; G06T 2207/10088
See application file for complete search history.

(56) References Cited

U.S. PATENT DOCUMENTS

| 7,652,474 B2 | 1/2010 | Griswold |
| 10,635,943 B1 | 4/2020 | Lebel |

(Continued)

FOREIGN PATENT DOCUMENTS

DE    102020209913 A1 *    7/2021

OTHER PUBLICATIONS

T. Jhamb. 2015. A Review on Image Reconstruction through MRI k-Space Data, I.J. Image, Graphics and Signal Processing, p. 42-59 (Year: 2015).*

(Continued)

*Primary Examiner* — Sean D Mattson
(74) *Attorney, Agent, or Firm* — Fletcher Yoder, P.C.

(57) ABSTRACT

A method for producing an image of a subject with a magnetic resonance imaging (MRI) comprises acquiring a first set of partial k-space data from the subject and generating a phase corrected image based on a phase correction factor and the first set of the partial k-space data. The method further includes transforming the phase corrected image into a second set of partial k-space data and reconstructing the image of the subject from the second set of the partial k-space data and a weighting function.

13 Claims, 9 Drawing Sheets

(56) References Cited

U.S. PATENT DOCUMENTS

| | | | |
|---|---|---|---|
| 2004/0258326 A1* | 12/2004 | Lee | G01R 33/561 |
| | | | 382/280 |
| 2014/0266192 A1* | 9/2014 | Taviani | G01R 33/4828 |
| | | | 324/309 |
| 2017/0178318 A1* | 6/2017 | Wang | G06T 7/0012 |
| 2020/0041592 A1 | 2/2020 | Huang | |
| 2020/0126190 A1 | 4/2020 | Lebel | |
| 2020/0202586 A1 | 6/2020 | Li | |
| 2020/0341101 A1* | 10/2020 | Splitthoff | G01R 33/56509 |

OTHER PUBLICATIONS

J. Pauly. 2005. Partial k-Space Reconstruction, p. 1-13 (Year: 2005).*

I. Fantini. 2018. Automatic Detection of Motion Artifacts on MRI Using Deep CNN, p. 1-4 (Year: 2018).*

L. Wu. 2020. Complex Imaging of Phase Domains by Deep Neural Networks, p. 12-21 (Year: 2020).*

K. Jin. 2016. A General Framework for Compressed Sensing and Parallel MRI Using Annihilating Filter Based Low-Rank Hankel Matrix, p. 480-495 (Year: 2016).*

J. Pauly, Partial k-Space Recconstruction, 2005, 1-13 (Year: 2005).*

I. Fantini, Automatic detection of motion artifacts on MRI using Deep CNN, IEEE, Jan. 4, 2018 (Year: 2018).*

T. Jhamb, A Review on Image Reconstruction through MRI k-Space Data, I.J. Image, Graphics and Signal Processing, Jul. 2015, 42-59 (Year: 2015).*

J. Pauly, Partial k-Space Recconstruction, Jan. 13, 2005 (Year: 2005).*

K.H. Jin, A General Framework for Compressed Sensing and Parallel MRI Using Annihilating Filter Based Low-Rank Hankel Matrix, IEEE Transactions on Computational Imaging, vol. 2, No. 4, Dec. 2016, 480-495 (Year: 2016).*

I. Fantini, Automatic detection of motion artifacts on MRI using Deep CNN, IEEE, 2018, 1-4 (Year: 2018).*

Paul et al., "Least-Squares FIR Models of Low-Resolution MR data for Efficient Phase-Error Compensation with Simultaneous Artefact Removal," https://arxiv.org/pdf/1303.2437; Mar. 11, 2013, 34 pages.

Antun et al., "On Instabilities of Deep Learning in Image Reconstruction and the Potential Cost of AI," PNAS 2020, 8 pages.

Blaimer et al., "Virtual coil concept for improved parallel MRI employing conjugate symmetric signals," MRM, 2009, 61: pp. 93-102, 10 pages.

Chang et al., "High-quality and self-navigated diffusion-weighted imaging enabled by a novel interleaved block-segmented (iblocks)," Proc ISMRM, 2015, Abstract Only, 1 page.

Cuppen et al., "Reducing MR Imaging Time by One-Sided Reconstruction," Magnetic Resonance Imaging, May 1987: pp. 516-527, 2 pages.

Haacke et al., "A Fast Iterative, Partial-Fourier Technique Capable of Local Phase Recovery", Journal of Magnetic Resonance, 1991, 92: pp. 126-145, 20 pages.

Huang et al., "Partial Fourier Reconstruction through Data Fitting and Convolution in k-Space," Magnetic Resonance in Medicine, 2009, 62: pp. 1261-1269, 9 pages.

Ju et al., "Ultrafast 3D Partial Fourier Reconstruction with Well-Preserved Phase using DNN," Proc ISMRM, 2019, pp. 4708, 3 pages.

Kadimesetty et al., "Optimal Partial Fourier MRI reconstruction: Homodyne vs POCS," Proc ISMRM, 2018, pp. 3521, 3 pages.

McGibney et al., "Quantitative Evaluation of Several Partial Fourier Reconstruction Algorithms Used in MRI," Partial Fourier Reconstruction Algorithms, University of Calgary, 1993, pp. 51-59, pages.

Muckley et al., "Learned Gibbs Removal in Partial Fourier Acquisitions for Diffusion MRI," Proc ISMRM, 2019, 3 pages.

Muckley et al., "Training a Neural Network for Gibbs and Noise Removal in Diffusion MRI," Magnetic Resonance in Medicine, Jul. 14, 2020, vol. 85, 18 pages.

Noll et al., "Homodyne Detection in Magnetic Resonance Imaging," IEEE Trans Med Imaging, Oct. 1991: pp. 154-163, 10 pages.

Paul et al., "Higher dimensional homodyne filtering for suppression of incidental phase artifacts in multichannel MRI," https://arxiv.org/ftp/arxiv/papers/1501/1501.03271.pdf, Jan. 14, 2015, 36 pages.

Pauly, "Partial k-Space Reconstruction," Stanford University, 2005, Chapter 2, pp. 11-24, 14 pages.

Toews et al., "Deep Partial Fourier Reconstruction," Proc ISMRM, 2019, pp. 4702, 3 pages.

Ueker et al., "Robust Partial Fourier Parallel Imaging Using ESPIRIT and Virtual Conjugate Coils," Proc ISMRM 2014, pp. 1629, 1 page.

Yan et al., "Data Truncation Artificat Reduction in MR Imaging Using a Multilayer Neural Network," IEEE Transactions on Medical Imaging, 1993, vol. 12, pp. 73-77, 5 pages.

* cited by examiner

SYSTEM AND METHOD FOR RECONSTRUCTION USING A HIGH-RESOLUTION PHASE IN MAGNETIC RESONANCE IMAGES

BACKGROUND

The field of the disclosure relates generally to systems and methods of magnetic resonance imaging (MRI), and more particularly, to techniques of image reconstruction in MRI.

MRI has proven useful in diagnosis of many diseases. MRI provides detailed images of soft tissues, abnormal tissues such as tumors, and other structures, which cannot be readily imaged by other imaging modalities, such as computed tomography (CT). Further, MRI operates without exposing patients to ionizing radiation experienced in modalities such as CT and x-rays.

The MR signals acquired with an MRI system are signal samples of the subject of the examination in Fourier space, or what is often referred to in the art as "k-space". In MR imaging, a partial k-space is often sampled in order to increase the efficiency of the acquisition and/or to suppress artifacts. Reconstructing a partially-sampled k-space dataset results in an image that is contaminated by truncation artifacts in the form of both blurring and a characteristic ringing that severely degrades the diagnostic value of the MR image.

Therefore, there is a need for an improved magnetic resonance imaging system and method.

BRIEF DESCRIPTION

In accordance with an embodiment of the present technique, a method for producing an image of a subject with a magnetic resonance imaging (MRI) system is presented. The method includes acquiring, a first set of partial k-space data from the subject and generating a phase corrected image based on a phase correction factor and the first set of the partial k-space data. The method further includes transforming the phase corrected image into a second set of partial k-space data and reconstructing the image of the subject from the second set of the partial k-space data and a weighting function.

In accordance with another embodiment of the present technique, a magnetic resonance imaging (MRI) system is presented. The MRI system includes a magnet configured to generate a polarizing magnetic field about at least a portion of a subject arranged in the MRI system and a gradient coil assembly including a plurality of gradient coils configured to apply at least one gradient field to the polarizing magnetic field. The MRI system also includes a radio frequency (RF) system configured to apply an RF field to the subject and to receive magnetic resonance signals from the subject. The MRI system further includes a processing system programmed to acquire a first set of partial k-space data from the subject. The processing system is also programmed to generate a phase corrected image based on a phase correction factor and the first set of the partial k-space data and transform the phase corrected image into a second set of partial k-space data. The processing system is further programmed to reconstruct the image of the subject from the second set of the partial k-space data and a weighting function.

In accordance with yet another embodiment of the present technique, a method of MR imaging is presented. The method includes acquiring a first set of k-space data for less than all of k-space from a subject and reconstructing the k-space data into a crude image. The method also includes generating a phase corrected image based on a phase correction factor and the first set of k-space data and transforming the phase corrected image into a second set of k-space data. The method further includes reconstructing, from the second set of the k-space data and a weighting function, the image of the subject.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present embodiments, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments. Furthermore, the terms "circuit" and "circuitry" and "controller" may include either a single component or a plurality of components, which are either active and/or passive and are connected or otherwise coupled together to provide the described function.

In magnetic resonance imaging (MRI), an object is placed in a magnet. When the object is in the magnetic field generated by the magnet, magnetic moments of nuclei, such as protons, attempt to align with the magnetic field but process about the magnetic field in a random order at the nuclei's Larmor frequency. The magnetic field of the magnet is referred to as B0 and extends in the longitudinal or z direction. In acquiring a MR image, a magnetic field (referred to as an excitation field B1), which is in the x-y plane and near the Larmor frequency, is generated by a radiofrequency (RF) coil and may be used to rotate, or "tip," the net magnetic moment $M_z$ of the nuclei from the z direction to the transverse or x-y plane. A signal, which is referred to as a MR signal, is emitted by the nuclei, after the excitation signal B1 is terminated. To use the MR signals to generate an image of an object, magnetic field gradient pulses ($G_x$, $G_y$, and $G_z$) are used. The gradient pulses are used to scan through the k space, the space of spatial frequencies or inverse of distances. A Fourier relationship exists between the acquired MR signals and an image of the object, and therefore the image of the object can be derived by reconstructing the MR signals. The images of the object may include two dimensional (2D) or three-dimensional (3D) images.

Figure 1:
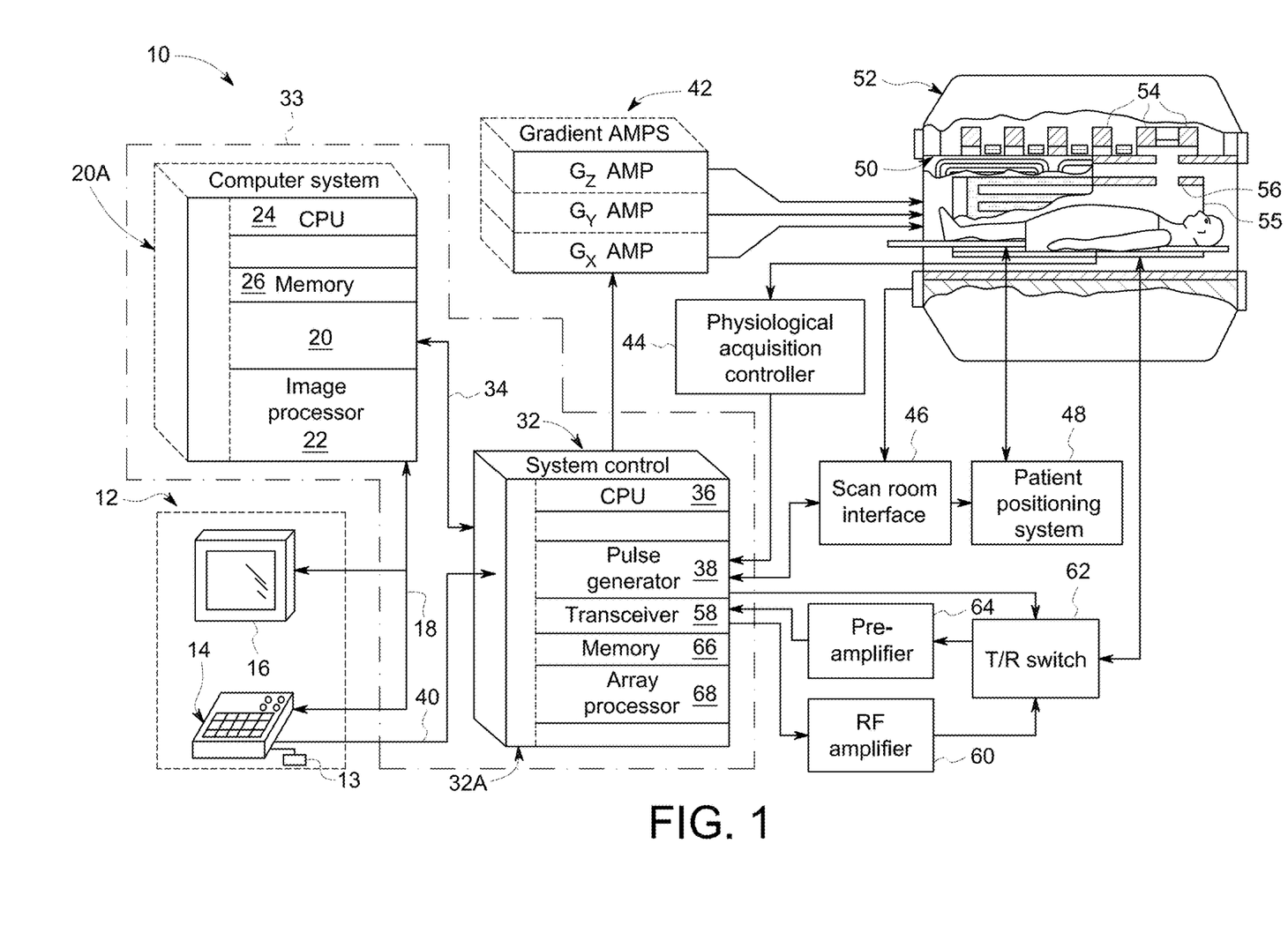
FIG. 1 is a schematic diagram of an exemplary magnetic resonance imaging (MRI) system.

Embodiments of the present disclosure will now be described, by way of an example, with reference to the figures, in which FIG. 1 is a schematic diagram of a magnetic resonance imaging (MRI) system 10. Operation of the system 10 may be controlled from an operator console 12, which includes an input device 13, a control panel 14, and a display screen 16. The input device 13 may be a mouse, joystick, keyboard, track ball, touch activated screen, light wand, voice control, and/or other input device. The input device 13 may be used for interactive geometry prescription. The console 12 communicates through a link 18 with a computer system 20 that enables an operator to control the production and display of images on the display screen 16. The link 18 may be a wireless or wired connection. The computer system 20 may include modules that communicate with each other through a backplane 20a. The modules of the computer system 20 may include an image processor module 22, a central processing unit (CPU) module 24, and a memory module 26 that may include a frame buffer for storing image data arrays, for example. The computer system 20 may be linked to archival media devices, permanent or back-up memory storage or a network for storage of image data and programs and communicates with MRI system control 32 through a high-speed signal link 34. The MRI system control 32 may be separate from or integral with the computer system 20. The computer system 20 and the MRI system control 32 collectively form an "MRI controller" 33 or "controller".

In the exemplary embodiment, the MRI system control 32 includes modules connected by a backplane 32a. These modules include a CPU module 36 as well as a pulse generator module 38. The CPU module 36 connects to the operator console 12 through a data link 40. The MRI system control 32 receives commands from the operator through the data link 40 to indicate the scan sequence that is to be performed. The CPU module 36 operates the system components to carry out the desired scan sequence and produces data which indicates the timing, strength and shape of the RF pulses produced, and the timing and length of the data acquisition window. The CPU module 36 connects to components that are operated by the MRI controller 32, including the pulse generator module 38 which controls a gradient amplifier 42, a physiological acquisition controller (PAC) 44, and a scan room interface circuit 46.

In one example, the CPU module 36 receives patient data from the physiological acquisition controller 44, which receives signals from sensors connected to the subject, such as ECG signals received from electrodes attached to the patient. The CPU module 36 receives, via the scan room interface circuit 46, signals from the sensors associated with the condition of the patient and the magnet system. The scan room interface circuit 46 also enables the MRI controller 33 to command a patient positioning system 48 to move the patient to a desired position for scanning.

A whole-body RF coil 56 is used for transmitting the waveform towards subject anatomy. The whole body-RF coil 56 may be a body coil. An RF coil may also be a local coil that may be placed in more proximity to the subject anatomy than a body coil. The RF coil 56 may also be a surface coil. RF coils containing RF receiver channels may be used for receiving the signals from the subject anatomy. Typical surface coil would have eight receiving channels; however, different number of channels are possible. Using the combination of both a body coil 56 and a surface coil is known to provide better image quality.

The pulse generator module 38 may operate the gradient amplifiers 42 to achieve desired timing and shape of the gradient pulses that are produced during the scan. The gradient waveforms produced by the pulse generator module 38 may be applied to the gradient amplifier system 42 having $G_x$, $G_y$, and $G_z$ amplifiers. Each gradient amplifier excites a corresponding physical gradient coil in a gradient coil assembly 50, to produce the magnetic field gradients used for spatially encoding acquired signals. Specifically, $G_x$ corresponds to a flow/frequency encoding gradient, $G_y$ corresponds to a phase encoding gradient and $G_z$ corresponds to a slice select gradient. The gradient coil assembly 50 may form part of a magnet assembly 52, which also includes a polarizing magnet 54 (which, in operation, provides a longitudinal magnetic field $B_0$ throughout a target volume 55 that is enclosed by the magnet assembly 52 and a whole-body RF coil 56 (which, in operation, provides a transverse magnetic field B1 that is generally perpendicular to B0 throughout the target volume 55. A transceiver module 58 in the MRI system control 32 produces pulses that may be amplified by an RF amplifier 60 and coupled to the RF coil 56 by a transmit/receive switch 62. The resulting signals emitted by the excited nuclei in the subject anatomy may be sensed by receiving coils (not shown) and provided to a preamplifier 64 through the transmit/receive switch 62. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the receiving coil during the receive mode.

The MR signals produced from excitation of the target are digitized by the transceiver module 58. The MR system control 32 then processes the digitized signals by Fourier transform to produce k-space data, which is transferred to a memory module 66, or other computer readable media, via the MRI system control 32. "Computer readable media" may include, for example, structures configured so that electrical, optical, or magnetic states may be fixed in a manner perceptible and reproducible by a conventional computer (e.g., text or images printed to paper or displayed on a screen, optical discs, or other optical storage media, "flash" memory, EEPROM, SDRAM, or other electrical storage media; floppy or other magnetic discs, magnetic tape, or other magnetic storage media).

A scan is complete when an array of raw k-space data has been acquired in the computer readable media 66. This raw k-space data is rearranged into separate k-space data arrays for each image to be reconstructed, and each of these k-space data arrays is input to an array processor 68, which operates to reconstruct the data into an array of image data, using a reconstruction algorithm such as a Fourier transform. When the full k-space data is obtained, it represents entire volume of the subject body and the k-space so obtained may be referred as the reference k-space. Similarly, when only the partial k-space data is obtained, the image may be referred as the partial k-space. This image data is conveyed through the data link 34 to the computer system 20 and stored in memory. In response to the commands received from the operator console 12, this image data may be archived in a long-term storage or may be further processed by the image processor 22 and conveyed to the operator console 12 and presented on the display 16.

MR signals are represented by complex numbers, where each location at the k-space is represented by a complex number, with I and Q quadrature MR signals being the real and imaginary components. Complex MR images may be reconstructed based on I and Q quadrature MR signals, using processes such as Fourier transform of the k-space MR data. Complex MR images are MR images with each pixel represented by a complex number, which also has a real component and an imaginary component. The magnitude M of the received MR signal may be determined as the square root of the sum of the squares of the I and Q quadrature components of the received MR signal as in Eq. (3) below:

$$M = \sqrt{I^2 + Q^2} \quad (1)$$

and the phase φ of the received MR signal may also be determined as in eq. (2) below:

$$\phi = \tan^{-1}\left(\frac{Q}{I}\right) \quad (2)$$

In MRI, asymmetric sampling in the frequency and phase encoding directions or dimensions is referred to as fractional echo and partial number of acquisition (NEX), respectively, and is widely used in both 2D and 3D MR imaging. These undersampling techniques are typically used to shorten echo times (e.g. to increase SNR or alter tissue contrast), to shorten repetition times (e.g. to reduce scan time), and/or to suppress unwanted artifacts (such as fineline artifact in fast-spin echo (FSE) imaging or off-resonance artifacts in gradient recalled echo (GRE) and echo planar imaging (EPI)). Asymmetric sampling of k-space introduces truncation artifacts into the reconstructed images, both in the form of blurring and ringing. Various image reconstruction techniques have been devised, therefore, for reconstructing partial k-space data, such as conjugate synthesis, homodyne, and projection onto convex sets (POCS). These known techniques rely on some intrinsic estimate of the underlying image phase, which can be subsequently removed (or "corrected"), allowing the synthesis of the missing or unsampled data based on the principle of Hermitian symmetry of real-valued signals. This phase estimate is often derived from the central, symmetrically-sampled portion of k-space, and is limited in several important ways. First, the phase estimate is contaminated by thermal noise, which is especially problematic in low-signal image regions and/or when this phase estimate performed on a per-channel (or per-view) basis. Secondly, this phase estimate is inherently band-limited, and must be further low-pass filtered upon application to prevent the introduction of additional truncation artifacts. Therefore, high spatial frequency phase information is not corrected, leaving residual blurring in the final reconstructed image. The application of this low-frequency phase estimate also tends to bias the noise in the reconstructed image, which would otherwise tend to be normally distributed. The appearance of this biased noise signal in the reconstructed image degrades the image contrast, especially in low-signal regions, and the altered distribution of this noise degrades noise-averaging performance (as in multi-NEX EPI-diffusion) and/or complicate downstream denoising efforts, which are generally based on an assumed noise model. Further, the known partial k-space reconstruction techniques tend to exhibit various strengths and weaknesses, and the choice of method tends to result in various performance tradeoffs. POCS, for example, tends to localize reconstruction artifacts, whereas homodyne tends to result in contrast errors. Finally, in the case of homodyne and conjugate synthesis, the phase information is discarded during reconstruction, making them unsuitable for phase-sensitive applications, such as Dixon chemical shift imaging, phase-sensitive inversion recovery imaging, and generation of phase-sensitive maps based on the phases of the images.

Figure 2:
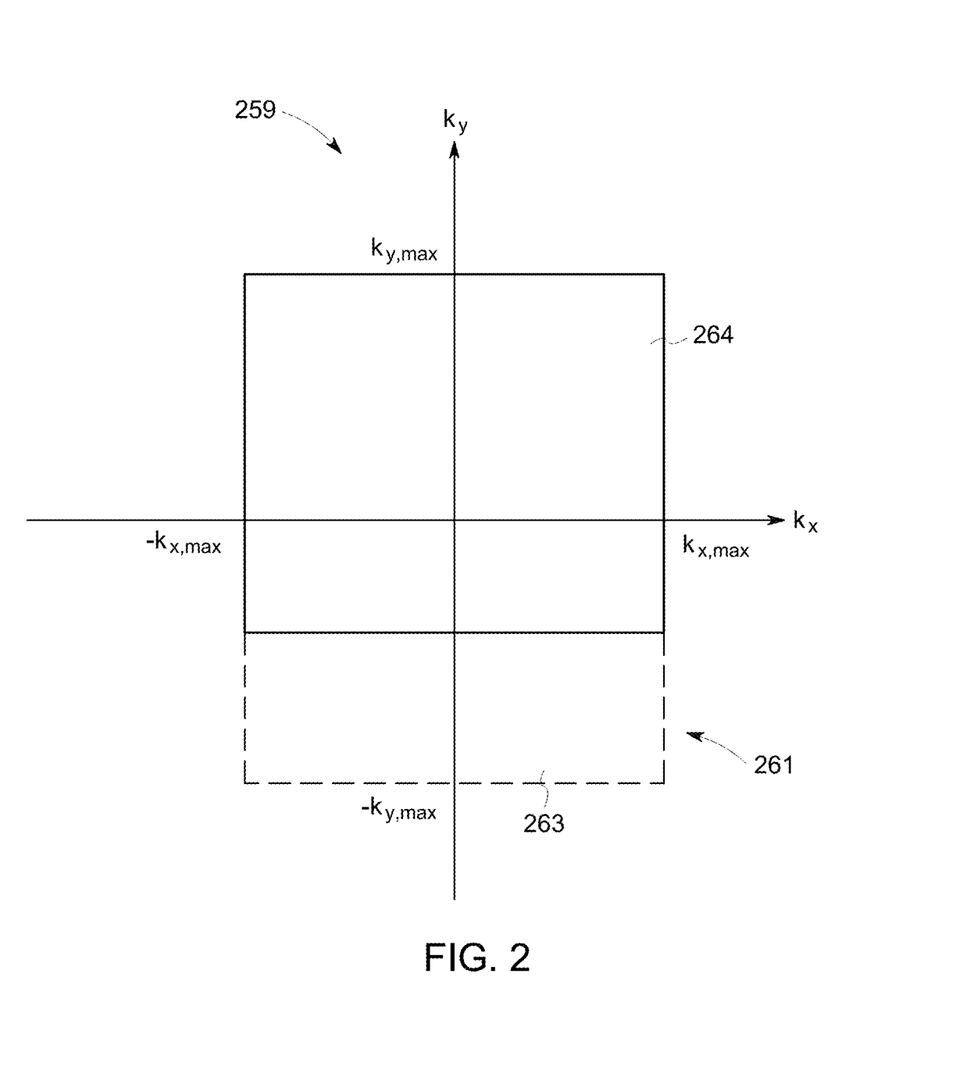
FIG. 2 is a schematic diagram of a partial k-space sampling, in accordance with an embodiment of the present technique.

FIG. 2 is a schematic diagram of a partial sampling pattern or truncation pattern 259 of a full k-space 261. A full k-space 261 is defined by the maximum kx or ky values $k_{x,max}$ and $k_{y,max}$, which is defined by maximum frequency- or phase-encoding gradients. In partial sampling, part of the high spatial frequency data 263 is not acquired. Truncation may be in the kx dimension and/or the ky dimension, and may be in the kz dimension in a three-dimension (3D) acquisition. The full k-space 261 is truncated into a partial k-space 264. The partial k-space 264 shown in FIG. 2 is the full k-space 261 truncated in the ky dimension, where negative high spatial frequency data are not acquired during the image acquisition of the partial k-space 264. Truncation may be asymmetrical, where the k-space is truncated asymmetrically in a dimension. The partial k-space 264 shown in FIG. 2 is asymmetrical truncated in the ky dimension. Truncation reduces high-spatial frequency data and causes truncation artifacts. Truncation along the axes of a 2D Cartesian coordinate system as shown in FIG. 2 is illustrated as an example only.

Figure 3:
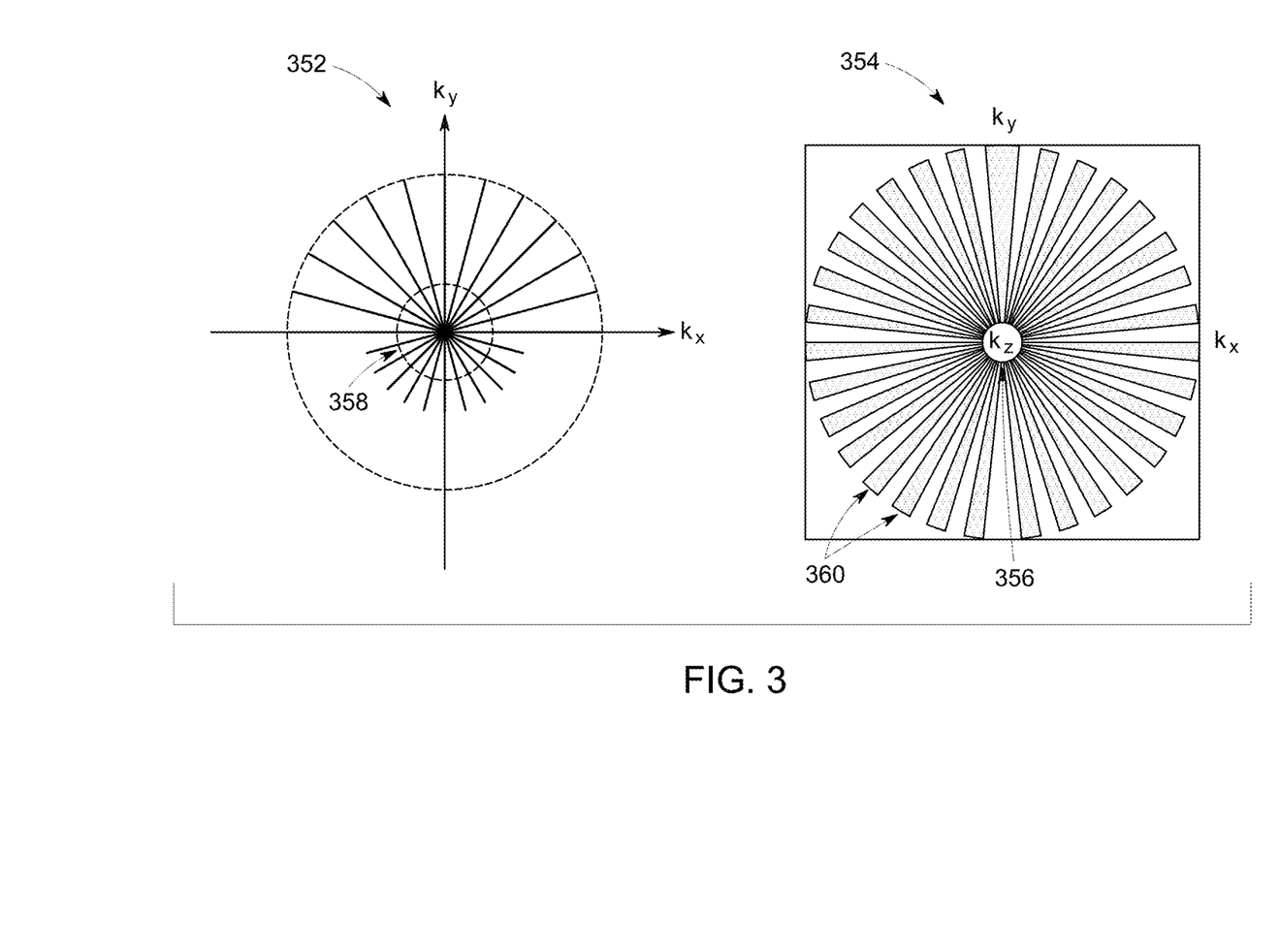
FIG. 3 is a schematic diagram of k-space sampling patterns, in accordance with an embodiment of the present technique.

FIG. 3 is a schematic diagram of k-space sampling patterns in accordance with an embodiment of the present technique. In FIG. 3, plot 352 shows a projection reconstruction acquisition whereas plot 354 shows a three-dimensional Fourier transformation (3DFT) acquisition. In general, the outer circles in both plots 352 and 354 relates to full acquisition/sampling or full k-space. However, plot 352 has only 2 planes $k_x$ and $k_y$, whereas plot 354 has 3 planes $k_x$, $k_y$ and $k_z$. The $k_x$ plane in plot 354 corresponds to an axis that will come out of the central dot 356. In general, in partial sampling, only a part of the high spatial frequency data is acquired which is represented by a smaller circle 358 in plot 352. Similarly, in plot 354, the data that is acquired is represented by the shaded bars 360. The systems and methods described herein may also be used for removal of truncation artifacts in images based on k-space data from a k-space that is asymmetrically truncated along the axes of a 2D/3D Cartesian coordinate system, a 2D/3D non-Cartesian coordinate system such as a polar, spherical, or cylindrical coordinate system, or a combination thereof. For example, the partial sampling pattern is the k-space being asymmetrically truncated in a radial dimension. In another example, the k-space data are acquired as a stack of radial lines in the $k_x$-$k_y$ planes along the $k_z$ direction and a partial sampling pattern is the k-space being asymmetrically truncated in a radial dimension in the $k_x$-$k_y$ plane and asymmetrically truncated in the $k_z$ dimension.

Figure 4:
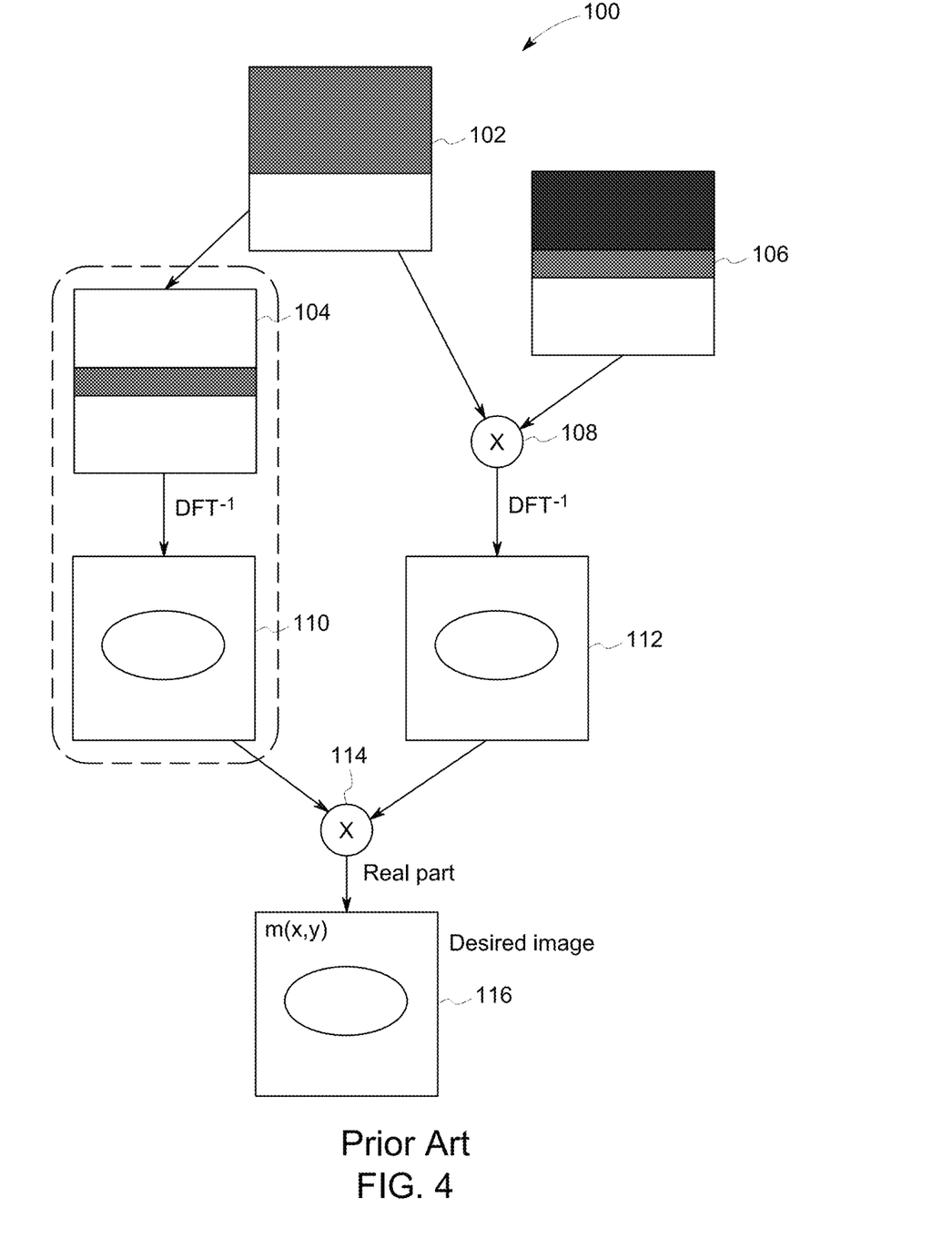
FIG. 4 is a schematic diagram of a conventional homodyne method for reconstructing partial k-space data.

FIG. 4 is a schematic diagram of a conventional homodyne method 100 for reconstructing partial k-space data. In method 100, initially a partial asymmetric k-space data set $M_{pk}(k_x, k_y)$ (102) and a central symmetric k-space data set $M_s(k_x, k_y)$ (104) is generated. As discussed earlier, a phase correction factor needs to be applied before the k-space symmetry can be exploited to synthesize the missing data from the partial k-space data $M_{pk}(k_x, k_y)$. This phase estimate is derived from the central, symmetrically-sampled k-space data $M_s(k_x, k_y)$.

Further, the method 100 includes defining a pre-weighting function $W(k_y)$ (106). The partial k-space data is then multiplied by the pre-weighting function by a multiplier block 108. The weighted partial k-space data from the multiplier block 108 is then inverse Fourier transformed to produce an weighted image $m_{pk}(x, y)*w(x, y)$ (112). Similarly, central symmetric k-space data set $M_s(k_x, k_y)$ is inverse Fourier transformed to produce the image $m_s(x, y)$ (110). The phase correction factor $p^*(x, y)$ is a unit amplitude/magnitude image with a phase that is the conjugate of $m_s(x, y)$ and is given as:

$$p^*(x,y)=e^{-i\Leftrightarrow m_s(x,y)} \quad (3)$$

The phase correction factor is then used to correct the weighted image by multiplying $p^*(x, y)$ with $m_{pk}(x, y)*w(x, y)$ by another multiplier block 114. A desired image 116 is then obtained by taking the real part of the result of the multiplier block 114.

As shown in FIG. 4, the conventional Homodyne reconstruction method uses low-resolution phase for phase correction, resulting in severe artifacts in regions with rapid phase change due to motion, chemical shift, air-tissue interfaces, etc. Therefore, the reconstruction method in the present invention derives a high-resolution denoised phase from zero-filled complex data with deep learning and/or other methods, then applies the high-resolution phase during the phase correction step to minimize these artifacts. It should be noted that the term high-resolution phase refers to a phase having high resolution compared to the phase determined with conventional Homodyne reconstruction method or the phase determined with centralized symmetric k-space data.

Figure 5:
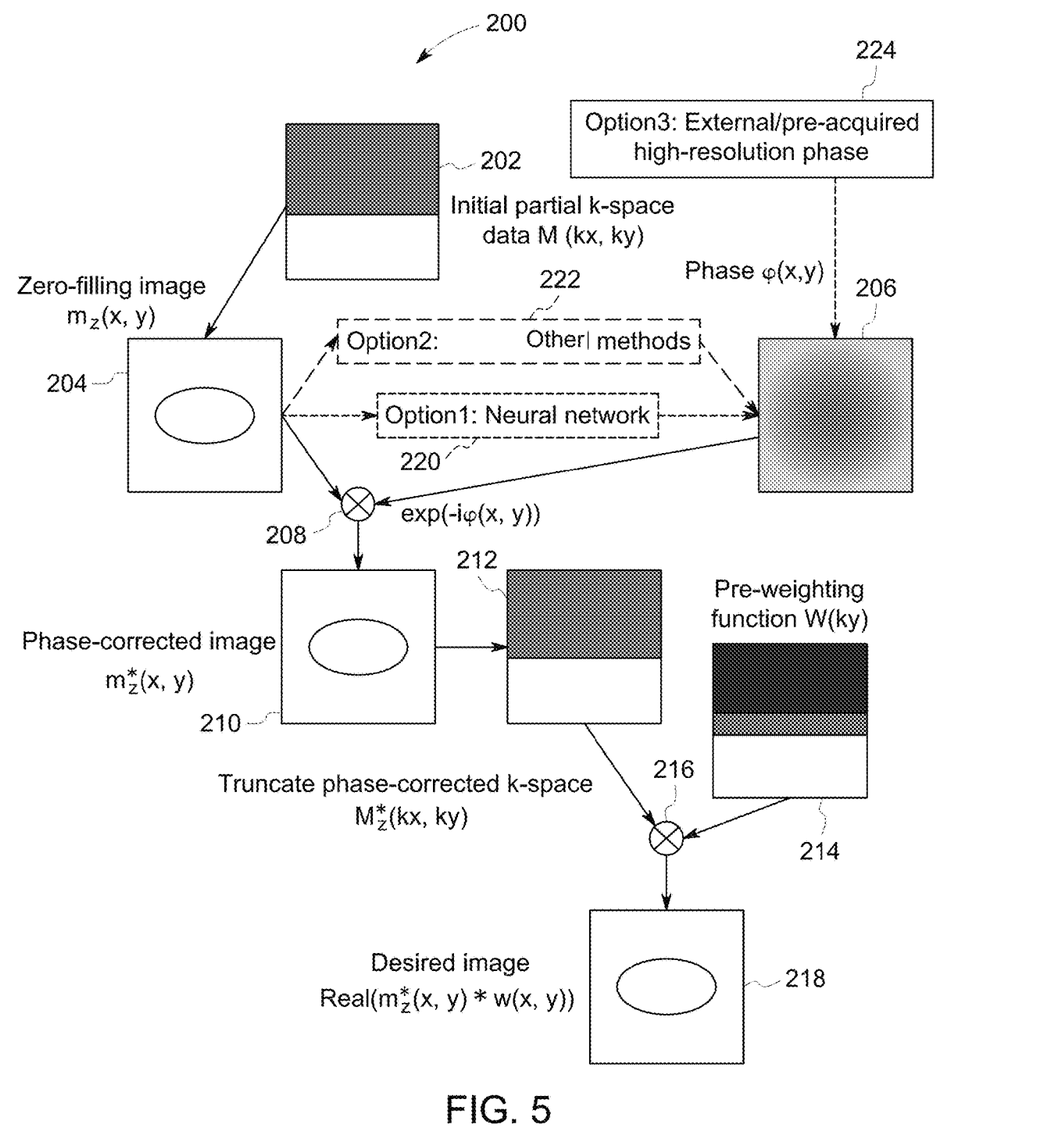
FIG. 5 is a schematic diagram of a method for reconstructing partial k-space data, in accordance with an embodiment of the present technique.

FIG. 5 is a schematic diagram of a method 200 for reconstructing partial k-space data, in accordance with an embodiment of the present technique. The method 200 may also be referred to as a modified homodyne reconstruction method. In method 200, initially a partial asymmetric k-space data set $M(k_x, k_y)$ i.e., a first set of partial k-space data 202 is generated. A crude image $m_z(x, y)$ 204 is then generated from the partial asymmetric k-space data set 202. The crude image 204 may be reconstructed by zero-filling the partial k-space data with zeros at locations corresponding to the skipped k-space locations to derive full k-space data, and then reconstructing the crude image based on the zero-filled k-space data. The full k-space data for the crude image may be reconstructed by methods other than zero-filling, such as interpolation.

The method further includes determining a high-resolution denoised phase $\varphi(x, y)$ 206. In one embodiment, the high-resolution denoised phase $\varphi(x, y)$ 206 is determined from the crude image 204 using deep learning (DL) techniques (e.g., a neural network 220). The high-resolution denoised phase 206 is determined in radians and may also be referred to as a phase correction factor. Besides DL methods, other denoising method 222 such as principal component analysis (PCA), Wavelet Analysis, Total Variance, etc.) may also be used to generate the high-resolution denoised phase 206. In yet another embodiment, the high-resolution denoised phase 206 may be determined using an external pre-acquired high resolution image 224. A multiplier block 207 multiplies the crude image with the high-resolution denoised phase to generate a phase corrected image $m_z^*(x, y)$ (210) given by:

$$m_z^*(x,y)=m_z(x,y)*e^{-I\Leftrightarrow\varphi(x,y)} \quad (4)$$

The phase corrected image 210 is then Fourier transformed to produce a truncated phase corrected k-space data set $M_z^*(k_x, k_y)$, i.e., a second set of partial k-space data 212. Further, the method 200 includes defining a pre-weighting function $W(k_y)$ (214). In general, the pre-weighting function is chosen to emphasize a subspace of the acquisition space or for a better reconstruction of a portion of the data. In one embodiment, the pre-weighting function represents spectral sampling density. In another embodiment, the pre-weighting function $W(k_y)$ may be determined as $$W(k_y) = \begin{cases} H(k_y) - k_{ymin} < k_y < k_{ymin} \\ 2k_{ymin} < k_y < k_{ymax} \\ 0 \; elsewhere \end{cases} \quad (6)$$

where $H(k_y)$ is a Hanning window. By way of example, the Hanning window can have a width of 4 $k_{ymin}$, that is centered around $k_{ymin}$, such as the following Hanning window:

$$H(k_y) = \frac{1}{2}\left(1 - \cos\left(\frac{2\pi k_y}{4.k_{ymin} - 1}\right)\right) \quad (7)$$

The phase corrected k-space data set 212 is then multiplied with the pre-weighting function 214 by a multiplier block 216. A desired image 218 is then obtained by taking the real part of the result of the multiplier block 216.

Figure 6:
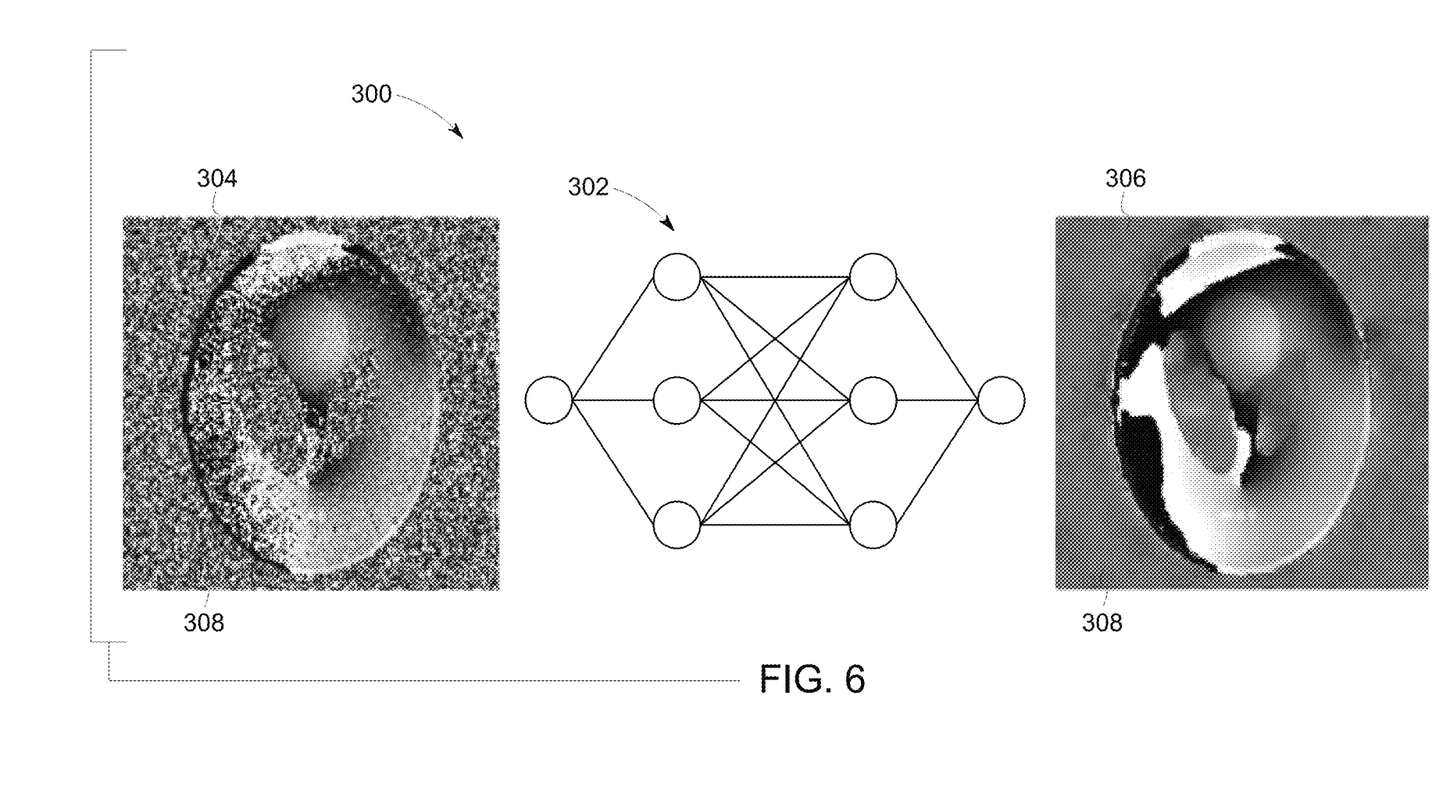
FIG. 6 is an exemplary neural network model for the method shown in FIG. 5, in accordance with an embodiment of the present technique.

FIG. 6 is a schematic diagram of an exemplary neural network model 300 that may be used in the embodiment of FIG. 5 for determining high-resolution denoised phase. The neural network model 300 may include a convolutional neural network 302. The neural network 302 accepts a MR phase image 304 contaminated with corrupted phase information (i.e., a corrupted image) and returns a pristine phase image 306, where the background phase 308 has been substantially denoised. Inputs and outputs to the neural network 302 may also be complex images, magnitude and phase image pairs, or real or imaginary image pairs. In one embodiment, the neural network 302 may trained with a loss function, which is a function measuring the inference error by the neural network 302. The loss function may be expressed as min(f1(input)−f2(output)), where f1 and f2 are functions of the input and the output to the neural network 302, respectively. In some embodiment, the loss function includes constraints based on prior knowledge of the phase information. For example, prior knowledge is that phase aliasing or phase wrapping may be caused by the computation method of phases. The phase calculated based on the equation of phase $$\Phi(x, y) = \tan^{-1}\left(\frac{Im(\hat{\rho}(x, y))}{Re(\hat{\rho}(x, y))}\right)$$

is limited to the range of [−π, η]. However, in real life, phases may be any real values. As a result, phases with addition of multiple 2π's appear as same phase values, causing phase aliasing. In phase sensitive imaging applications, where phase is used to encode a physical phenomenon, such as flow, motion, or temperature, prior knowledge includes physical law. Phase that behaves against physical law is penalized by the loss function. For example, in flow imaging or quantitative susceptibility measurements (QSM), flow is divergence free. In thermal imaging, heat is expected to dissipate relatively uniformly. For displacement imaging such as elastography, the displacement is expected to obey physical law of motion.

Figure 7A:
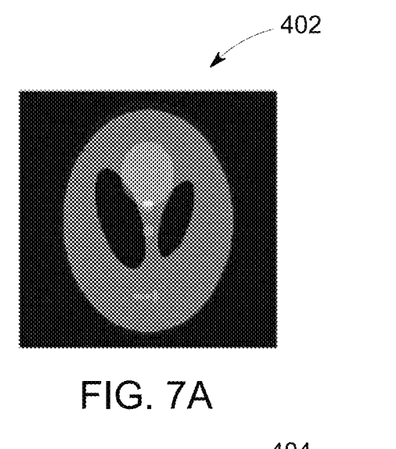
FIG. 7A is a phantom image corresponding to a fully sampled k-space data.
Figure 7B:
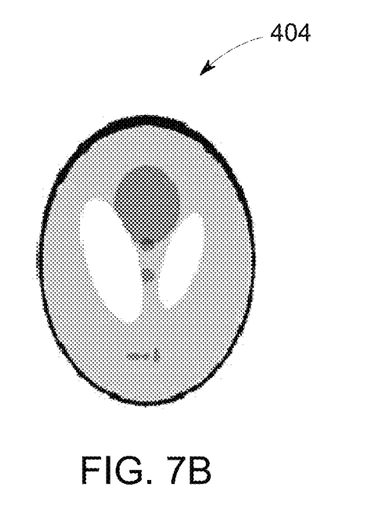
FIG. 7B is a phase image of the phantom image of FIG. 7A.
Figure 7C:
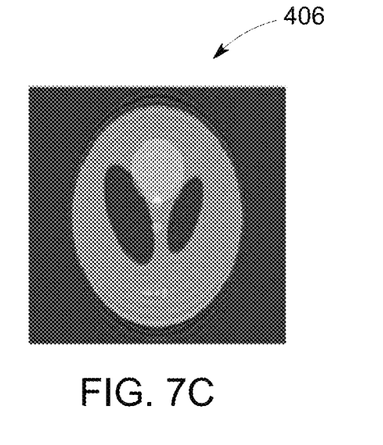
FIG. 7C is a zero filled phantom image corresponding to a partial k-space data set.
Figure 7D:
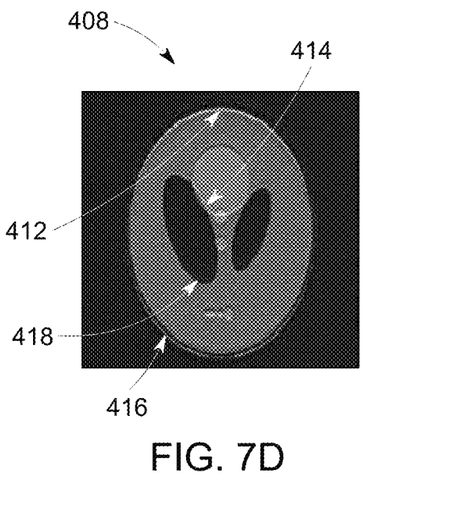
FIG. 7D is a phantom image after phase correction corresponding to a conventional homodyne method.
Figure 7E:
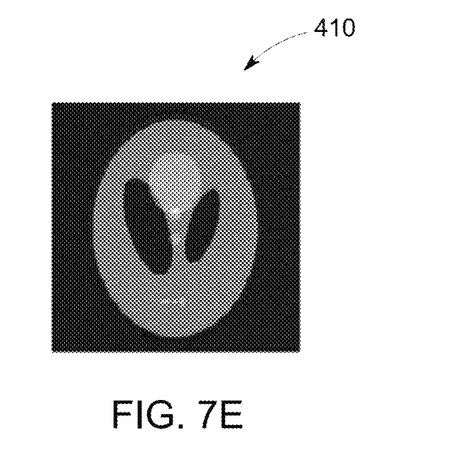
FIG. 7E is a phase corrected phantom image according to the modified homodyne technique, in accordance with an embodiment of the present technique.

FIGS. 7A-7E provide a comparison of k-space data reconstruction using conventional homodyne method with the modified homodyne technique presented herein. FIG. 7A is a phantom image 402 corresponding to a fully sampled k-space. FIG. 7B is a phase image 404 of the phantom image 402. FIG. 7C is a zero filled phantom image 406 corresponding to a partial k-space data set. FIG. 7D is a phantom image 408 after phase correction corresponding to a conventional homodyne method as described in FIG. 5. Further, FIG. 7E is a phase corrected phantom image 410 according to the modified homodyne technique presented herein. It should be noted that all the images presented in FIGS. 7A-7E are simulated phantom images. As can be seen from FIG. 7D, the phantom image 408 generated with the conventional homodyne method includes artifacts 412, 414, 416 and 418 corresponding to the regions of rapid phase change. These artifacts are minimized in the phantom image 410 (FIG. 7E) generated with the proposed modified Homodyne reconstruction method which looks very similar to the phantom image 402 generated with fully sampled k-space.

Figure 8A:
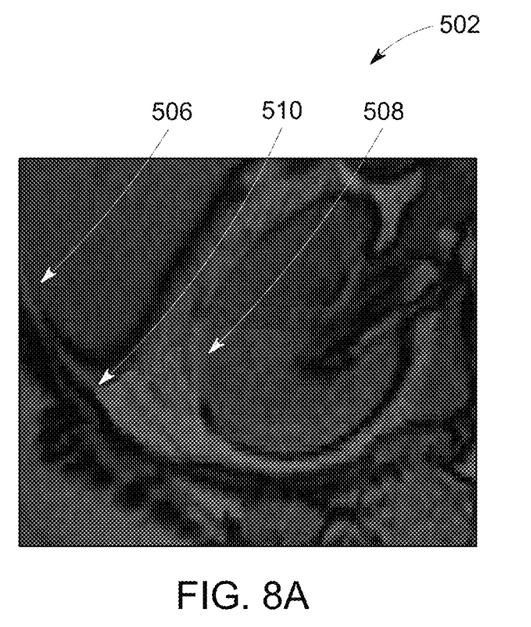
FIG. 8A is a simulated abdominal image after phase correction corresponding to a conventional homodyne method.
Figure 8B:
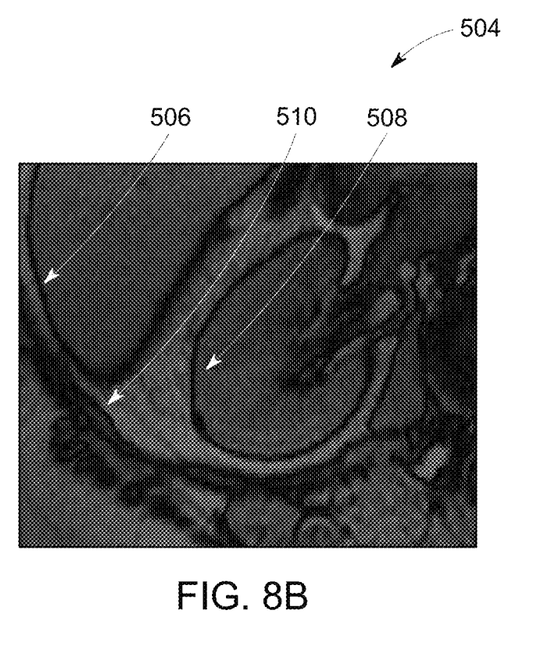
FIG. 8B is a phase corrected simulated abdominal image according to the modified homodyne technique, in accordance with an embodiment of the present technique.

FIGS. 8A-8B provide another comparison of k-space data reconstruction using conventional homodyne method with the modified homodyne technique presented herein. FIG. 8A is a simulated abdominal image 502 after phase correction corresponding to a conventional homodyne method as described in FIG. 5. Further, FIG. 8B is a phase corrected simulated abdominal image 504 according to the modified homodyne technique presented herein. As can be seen from, the artifacts 506, 508, 510 corresponding to rapid phase change in FIG. 8A have been minimized to a great extent in image 504 of FIG. 8B. In other words, the abdominal image generated using the conventional Homodyne is quite inferior to the abdominal image of the modified Homodyne technique with high resolution phase according to an embodiment of the present technique.

Figure 9:
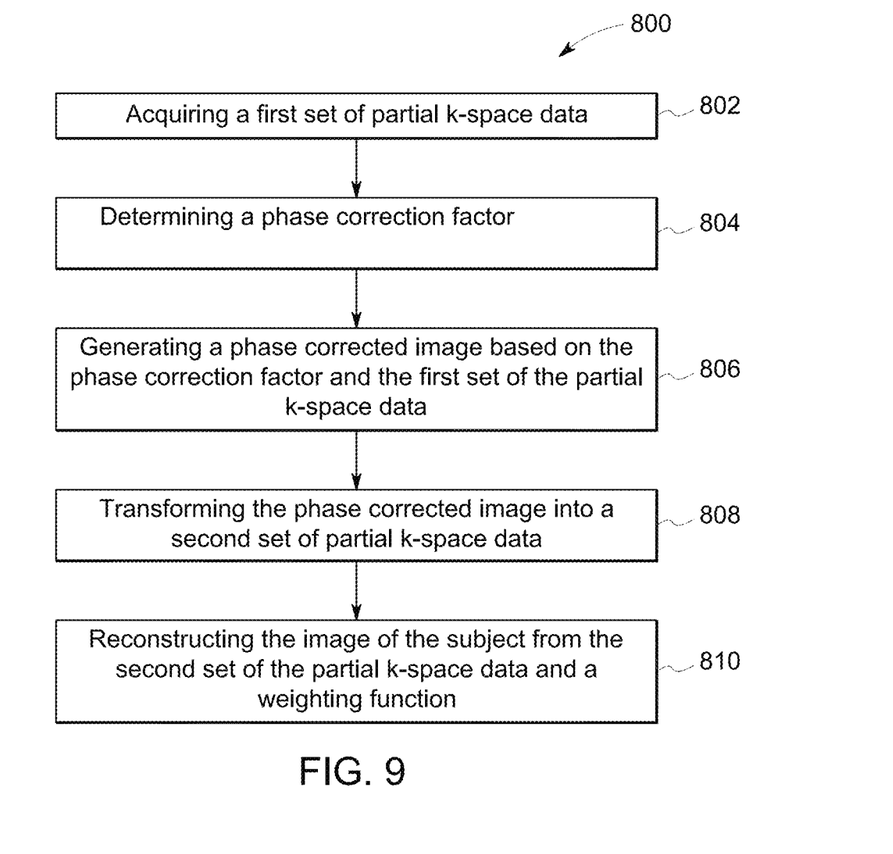
FIG. 9 is a flow chart depicting a method for producing an image of a subject with a magnetic resonance imaging (MRI) system, in accordance with an embodiment of the present technique.

FIG. 9 is a flow chart 800 depicting a method for producing an image of a subject with a magnetic resonance imaging (MRI) system. The method includes acquiring a first set of partial k-space data from the subject at step 802. In one embodiment, the first set of k-space data is for less than all of k-space from the subject. In other words, the first set of partial k-space data include k-space data from a partial k-space that is truncated in at least one k-space dimension. At step 804, the method includes determining a phase correction factor. The phase correction factor may be determined from the first set of the partial k-space data. To determine the phase correction factor from the partial k-space data, first a crude image is reconstructed from the first set of the partial k-space data. In one embodiment, the crude image is reconstructed by zero-filling the first set of partial k-space data with zeros at locations corresponding to the skipped k-space locations to derive full k-space data, and then reconstructing the crude image based on the zero-filled k-space data.

Thereafter, one of a neural network model, a wavelet transform algorithm, a principal component analysis (PCA) algorithm or a total variance (TV) algorithm is used with the crude image to determine the phase correction factor. In one embodiment, the neural network model is trained with a pair of pristine images and corrupted images, wherein the corrupted images include corrupted phase information, the pristine images are the corrupted images with the corrupted phase information reduced. In another embodiment, the phase correction factor may be determined from an external image which is a pre-acquired high resolution image. Further, the crude image and the phase correction factor is multiplied to generate a phase corrected image at step 806. At step 808, the method includes transforming the phase corrected image into a second set of partial k-space data. The transformation may be performed by applying a Fast Fourier Transform (FFT) on the phase corrected image.

At step 810, the method includes reconstructing the image of the subject, from the second set of the partial k-space data and a weighting function. In one embodiment, the weighting function refers to spectral sampling density and may include a Hanning window function. First, the weighting function is multiplied with the second set of the partial k-space data to and then the real portion of the result is used as the desired image of the subject.

One advantage of the present technique is that it systematically minimizes common artifacts in MRI images such as in regions with rapid phase variations and can be broadly applied to improve the image quality of out-of-phase water-fat imaging, diffusion imaging, gradient echo imaging, etc. Further, since the technique uses a partial k-space data, efficiency of the MRI acquisition is improved.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for producing an image of a subject with a magnetic resonance imaging (MRI) system, the method comprising:
   acquiring, using the MRI system, a first set of partial k-space data from the subject, wherein the first set of the partial k-space data is asymmetric and truncated in at least one k-space dimension;
   zero-filling the first set of the partial k-space data with zeros at locations corresponding to skipped k-space locations to derive full k-space data;
   reconstructing a first image based on the zero-filled k-space data;
   determining a phase correction factor from the first image;
   generating a phase corrected image based on the phase correction factor and the first set of the partial k-space data;
   transforming the phase corrected image into a second set of partial k-space data; and
   reconstructing, from the second set of the partial k-space data and a weighting function, the image of the subject.

2. The method of claim 1, comprises using a neural network model with the first image to determine the phase correction factor.

3. The method of claim 2, wherein the neural network model is trained with a pair of pristine images and corrupted images, wherein the corrupted images include corrupted phase information, the pristine images are the corrupted images with the corrupted phase information reduced.

4. The method of claim 2, wherein the neural network model is trained with a loss function including a constraint based on prior knowledge of phase information.

5. The method of claim 1, wherein generating the phase corrected image based on the phase correction factor and the first set of the partial k-space data comprises multiplying the first image with the phase correction factor.

6. The method of claim 1, wherein the image of the subject is reconstructed by determining a real portion of a multiplication result of the weighting function and the second set of the partial k-space data.

7. The method of claim 1, wherein the weighting function represents a spectral sampling density.

8. A magnetic resonance imaging (MRI) system, comprising:
   a magnet configured to generate a polarizing magnetic field about at least a portion of a subject arranged in the MRI system;
   a gradient coil assembly including a plurality of gradient coils configured to apply at least one gradient field to the polarizing magnetic field;
   a radio frequency (RF) system configured to apply an RF field to the subject and to receive magnetic resonance signals from the subject; and
   a processing system programmed to:
      acquire a first set of partial k-space data from the subject, wherein the first set of partial k-space data is asymmetric and truncated in at least one k-space dimension;
      zero-fill the first set of the partial k-space data with zeros at locations corresponding to skipped k-space locations to derive full k-space data;
      reconstruct a first image based on the zero-filled k-space data;
      determine a phase correction factor from the first image;
      generate a phase corrected image based on the phase correction factor and the first set of the partial k-space data;
      transform the phase corrected image into a second set of partial k-space data; and
      reconstruct, from the second set of the partial k-space data and a weighting function, the image of the subject.

9. The MRI system of claim 8, wherein the processing system is programmed to determine the phase correction factor from the first image using a neural network model.

10. The MRI system of claim 9, wherein the processing system is programmed to train the neural network model with a pair of pristine images and corrupted images, wherein the corrupted images include corrupted phase information, the pristine images are the corrupted images with the corrupted phase information reduced.

11. A method of MR imaging, comprising:
   acquiring a first set of k-space data for less than all of k-space from a subject, wherein the first set of the k-space data is asymmetric and truncated in at least one k-space dimension;
   zero-filling the first set of the k-space data with zeros at locations corresponding to skipped k-space locations to derive full k-space data;
   reconstructing a first image based on the zero-filled k-space data;
   determining a phase correction factor from the first image;
   generating the phase corrected image based on a phase correction factor and the first set of the k-space data;
   transforming the phase corrected image into a second set of k-space data; and
   reconstructing, from the second set of the k-space data and a weighting function, the image of the subject.

12. The method of claim 11, comprising determining the phase correction factor from the first image using ene of a neural network model.

13. The method of claim 12, wherein the neural network model is trained with a pair of pristine images and corrupted images, wherein the corrupted images include corrupted phase information, the pristine images are the corrupted images with the corrupted phase information reduced.

* * * * *